United States Patent [19]
Bossart et al.

[11] Patent Number: 5,370,004
[45] Date of Patent: Dec. 6, 1994

[54] MULTIPLE PORT PERSONAL AIR SAMPLING APPARATUS

[75] Inventors: Clayton J. Bossart, Monroeville; Daniel E. Bruce, Murrysville; Charles H. Etheridge, Pittsburgh, all of Pa.

[73] Assignee: Mine Safety Appliances Company, Pittsburgh, Pa.

[21] Appl. No.: 68,318

[22] Filed: May 26, 1993

Related U.S. Application Data

[63] Continuation of Ser. No. 938,292, Aug. 31, 1992, abandoned.

[51] Int. Cl.$^5$ ............................................. G01N 1/24
[52] U.S. Cl. ................................ 73/863.23; 73/863.33
[58] Field of Search ............. 73/863.21, 863.23, 863.25, 73/863.31–863.33, 864.15, 864.17, 864.18, 864.34, 866.5

[56] References Cited

U.S. PATENT DOCUMENTS

| | | | |
|---|---|---|---|
| 3,765,247 | 10/1973 | Riggs | 73/863.33 |
| 4,350,037 | 9/1982 | Higham | 73/863.21 |
| 4,532,814 | 8/1985 | Lali | 73/864.34 |
| 4,721,517 | 1/1988 | Cloutier | 73/863.23 |
| 4,858,476 | 8/1989 | Tobin | 73/863.33 |
| 4,993,271 | 2/1991 | Vargason | 73/863.33 |
| 5,119,682 | 6/1992 | Bellinger | 73/863.33 |

FOREIGN PATENT DOCUMENTS 2013682 10/1971 Germany ............................ 73/863.33

Primary Examiner—Robert Raevis
Attorney, Agent, or Firm—James G. Uber

[57] ABSTRACT

A personal sampling apparatus having multiple sampling ports for simultaneously taking a plurality of ambient air samples in parallel. Incorporated into the sampling apparatus is a regulator for enabling the apparatus to function with virtually any personal sampling pump. The regulator by being located immediately proximate to the sampling ports is able to provide independent vacuum flow rate control of each of the multiple sampling ports.

19 Claims, 5 Drawing Sheets

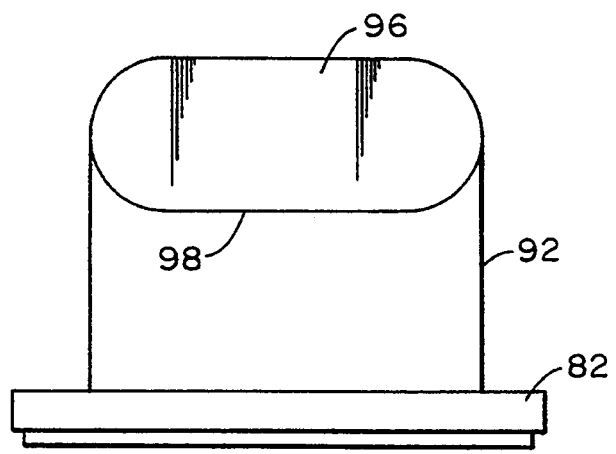
FIG. 6
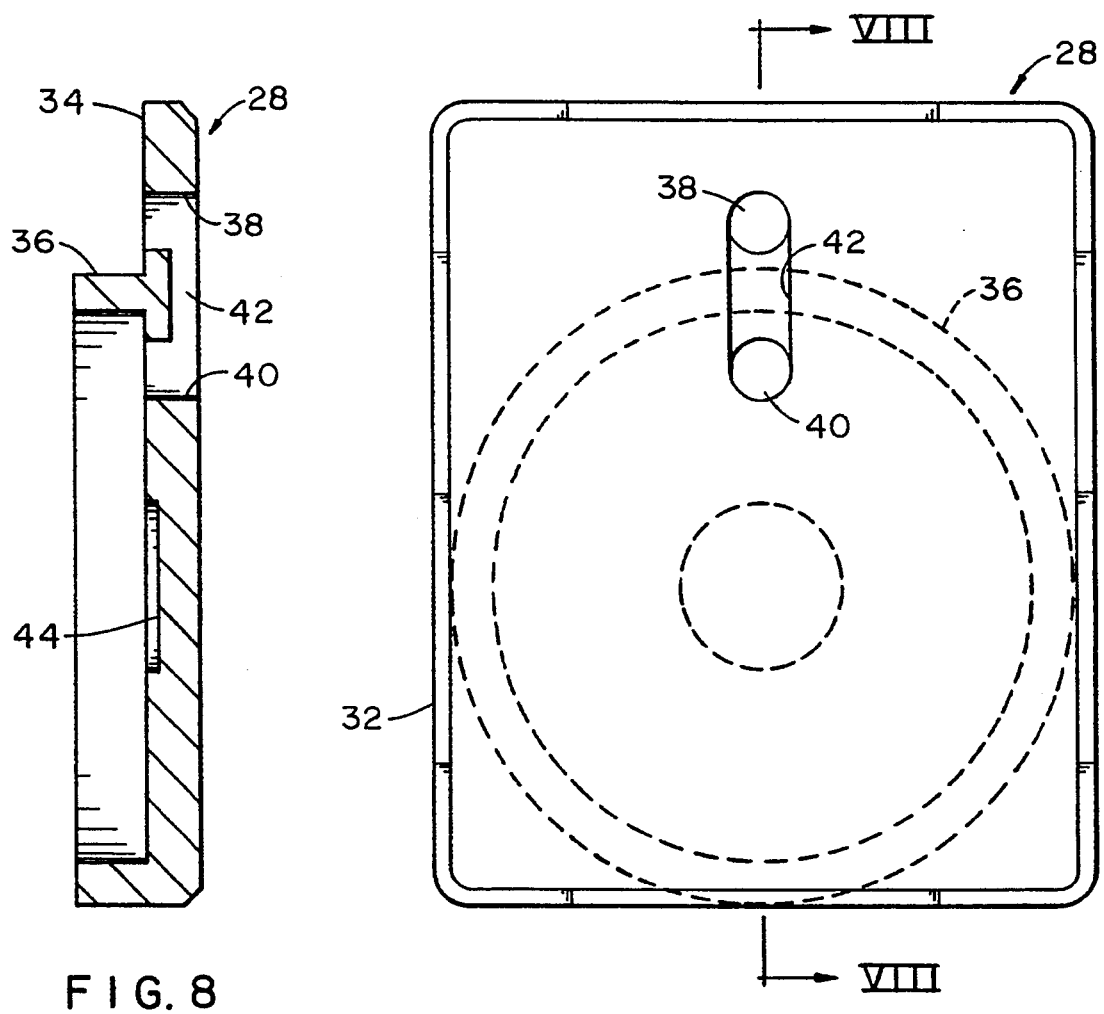
FIG. 8
FIG. 7

MULTIPLE PORT PERSONAL AIR SAMPLING APPARATUS

This is a continuation of copending application Ser. No. 07/938,292 filed on Aug. 31, 1992, now abandoned.

FIELD OF THE INVENTION

The present invention relates in general to air sampling equipment and, in particular, to a multiple port personal air sampling apparatus for simultaneously taking a plurality of ambient air samples in parallel.

BACKGROUND OF THE INVENTION

Air sampling apparatus for collecting airborne contaminants such as toxic mists, dusts, particulates, gases and vapors are known. Typically, such equipment is connected to a source of vacuum, e.g., a pump, whereby the airborne contaminants may be drawn into the equipment through the action of the pump. The pumps associated with air sampling equipment, commonly known as personal sampling pumps, are lightweight and portable such that they may be conveniently worn by an industrial hygienist or other worker that must perform activity in environments whose ambient air may be contaminated and/or hazardous.

Some air sampling apparatus are capable of simultaneously taking multiple air samples in parallel. Early versions of instruments of this type possessed no means for independently controlling individual sampling port vacuum flow rate. As a result, adjustment of the vacuum flow rate of one sampling port in such devices disturbed the vacuum flow rates previously set for the other sampling ports. In presently available parallel sampling apparatus, controlling the flow rates of the sampling ports is incorporated as part of the sampling pump. Consequently, the sampling apparatus of this latter class are capable of fitting and functioning with only one specific pump. Moreover, the remote location of the sampling ports from the regulator makes the vacuum flow rate partially dependent on the diameter and the length of the sample line connecting them. Depending on the flow rates in the sampling ports and the pressure drop in the sample line, these apparatus often require an iterative process to set and balance the flows through the sampling ports.

A need exists, therefore, for a multiple sampling port personal air sampling apparatus capable of simultaneously taking a plurality of independently controllable ambient air samples in parallel. This can be accomplished if the regulator for controlling individual sampling port vacuum is incorporated into the sampling apparatus rather than in the sampling pump associated therewith. So constructed, such apparatus would be capable of functioning with virtually any personal sampling pump while enabling independent control of each of the multiple sampling ports. Further, the apparatus would provide enhanced control and adjustability by regulating air flow essentially at the load site, i.e., proximate the sampling ports, rather than at a more remote location such as at the pump.

SUMMARY OF THE INVENTION

The present invention relates to an air sampling apparatus for use with a vacuum pump. The air sampling apparatus comprises a regulator including a regulator body having a discharge passageway and a fitting for enabling connection of the discharge passageway to the vacuum pump through a tube or hose. The regulator keeps the discharge passageway at a constant pressure. The apparatus further comprises a plurality of sampling ports provided in the regulator body that are communicable with the discharge passageway. A plurality of valves control communication between the sampling ports and the discharge passageway, whereby the plurality of valves are each selectively adjustable to permit independent air flow rates through each of the plurality of sampling ports due to the fixed pressure in the discharge passageway at the outlet of each valve.

The sampling apparatus is capable of simultaneously taking a plurality of ambient air samples in parallel and may be used with virtually any personal sampling pump. The apparatus enables independent control of each of the sampling ports and provides enhanced control and adjustability by regulating flow essentially at the load site, i.e., in the discharge passageway at the outlet of the control valves and proximate the sampling ports, rather than at a more remote location such as at the pump. In the present invention, the outlets of the valves are at a fixed and constant pressure due to the proximity of the regulator and because of the fixed pressure at its outlet, the flow rate through each valve is independent of the flow in the other valves.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings, wherein:

FIG. 6 is an elevational view of a sample tube pressure plate of the multiple port personal sampling apparatus of the present invention;

FIG. 7 is an elevation view of a diaphragm pressure plate of the multiple port personal sampling apparatus of the present invention; and FIG. 8 is a sectional view of the diaphragm pressure plate of FIG. 7 taken along line VIII—VIII thereof.

DETAILED DESCRIPTION OF THE INVENTION

Figure 1:
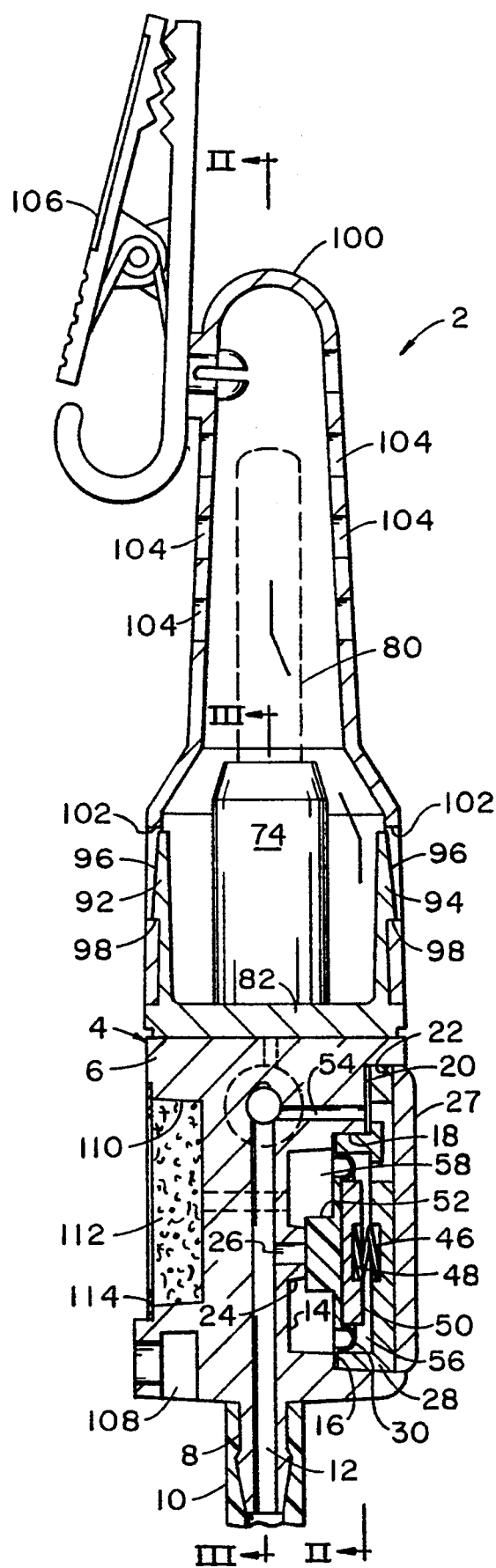
FIG. 1 is an elevational section view of a multiple port personal air sampling apparatus constructed in accordance with a preferred embodiment of the present invention.

With reference to FIG. 1, there is shown a presently preferred embodiment of a personal sampling apparatus 2 constructed according to the present invention. Apparatus 2 comprises a regulator 4 including a regulator body 6 formed of rigid material, e.g., metal or plastic. Regulator body 6 is provided with a fitting 8 which is adapted for connection to a conduit 10 (typically flexible plastic tubing) which connects the apparatus to an unillustrated remote source of vacuum such as a conventional personal sampling pump. For present purposes, such pump should preferably be capable of producing a 1.5 lpm vacuum flow rate at a load of 25 inches of water column. Although virtually any personal sampling pump having suitable pumping characteristics may be used in conjunction with the personal sampling apparatus 2, a preferred class of pumps include the family of Flow-Lite ™ pumps manufactured by the Mine Safety Appliances Company of Pittsburgh, Pa.

Figure 2:
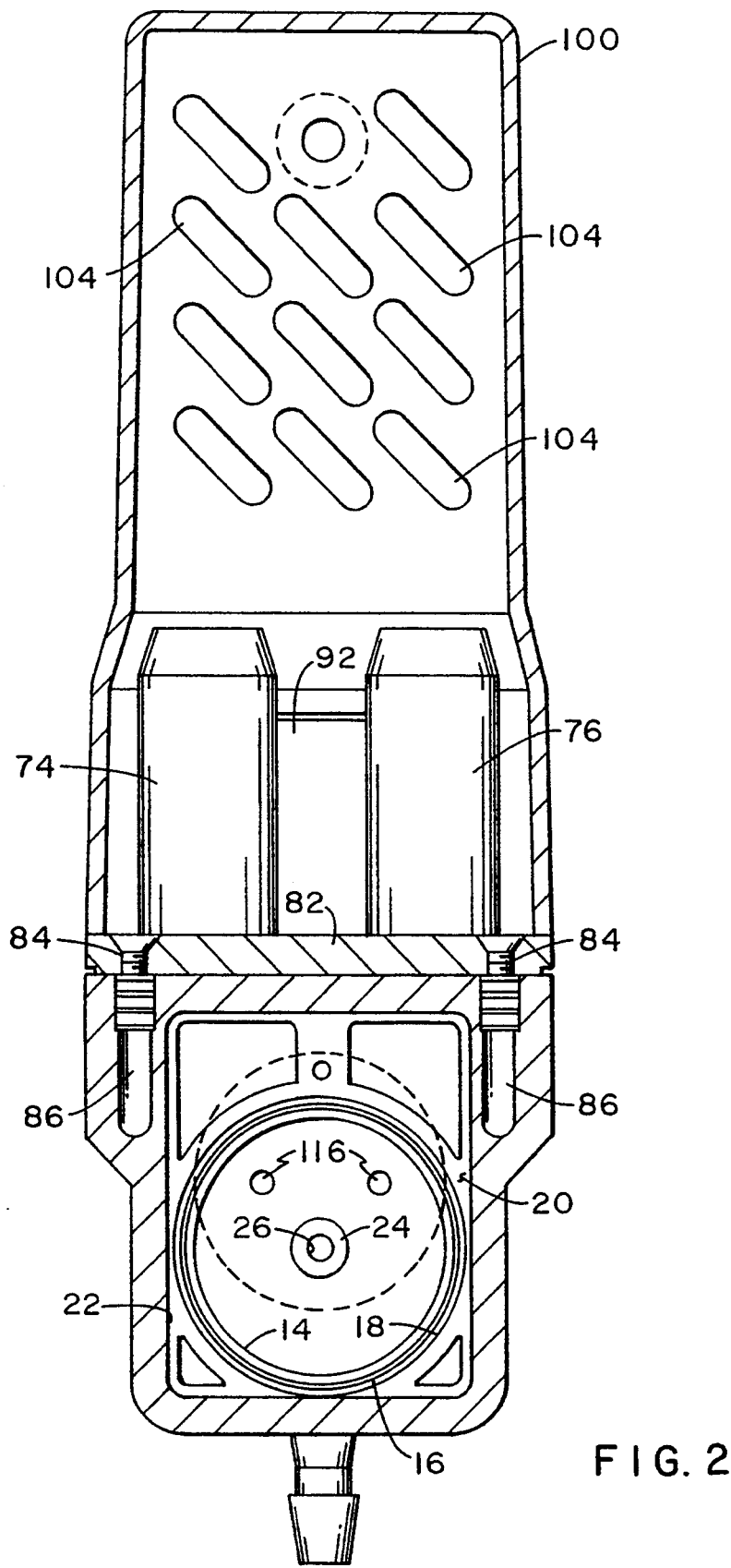
FIG. 2 is a view taken along line II—II of FIG. 1.

Provided within regulator body 6 is a discharge passageway 12 through which ambient air drawn into the apparatus 2 passes, in cooperation with fitting 8 and conduit 10, to the inlet of an unillustrated personal sampling pump. Reference to FIGS. 1 and 2 in combination reveals that one side of the regulator body 6 is formed with a series of cavities of progressively increasing size extending from the interior of the regulator body toward the exterior thereof. The first and innermost of these cavities is preferably generally circular in configuration and is identified herein by numeral 14. A first shoulder 16 is provided between the first cavity 14 and a second generally circular cavity 18 of slightly larger diameter than cavity 14; whereas, a second shoulder 20 is formed between the second cavity and an outermost and substantially larger, generally rectangular third cavity 22. Projecting from a central region of the first cavity 14 is a raised seat 24 that is provided with a first bore 26 which is in communication with discharge passageway 12. A cover plate 27 encloses cavity 22 and a diaphragm retainer plate 28. Diaphragm retainer plate 28, in turn, compressively retains a peripheral flange of a flexible diaphragm 30 against the first shoulder 16.

FIGS. 7 and 8 depict on an enlarged scale the preferred configuration of the diaphragm retainer plate 28. Reference to FIG. 7 in particular reveals that plate 28 is of a substantially rectangular shape and sized to be matingly received within cavity 22. The periphery 32 of plate 28 is continuously affixed to cavity 22 by a curable adhesive whereby an airtight seal is created therebetween. Projecting from an inner surface 34 (FIG. 8) of plate 28 is a circular ring 36 sized to be matingly received within cavity 18. The ring 36 serves as an abutment for retaining the diaphragm 30 against shoulder 16. A pair of spaced-apart parallel bores 38 and 40 straddle ring 36 and are connected by a channel 42, the functions of which bores and channel will be described in greater detail hereinbelow. A socket 44 is formed in the inner surface 34 of the diaphragm retainer plate 28. Socket 44 receives one end of a compression spring 46 (FIG. 1).

The opposite end of the spring 46 is shown received in a socket 48 of a diaphragm pressure plate 50 which contacts one face of the diaphragm 30. The opposite face of the diaphragm is provided with a stop member 52 which is biased into contact with raised seat 24 by spring 46. As will be described later herein, vacuum forces created within the regulator 4 by action of the personal sampling pump may, depending upon manipulation of certain controls, operate to lift the stop member 52 from raised seat 24, against the biasing force of spring 46, so as to permit air flow through bore 26.

A second bore 54 connects discharge passageway 12 with the bores 38 and 40 and channel 42 of the diaphragm retainer plate 28 so as to create a first pressure chamber 56 at one side of diaphragm 30. A second pressure chamber 58 is thus created at the other side of the diaphragm, the volume of the second pressure chamber consisting essentially of that of the first cavity 14. The function of the first and second pressure chambers 56 and 58 will be appreciated from the explanation of the operation of the air sampling apparatus 2 presented hereinafter.

Figure 3:
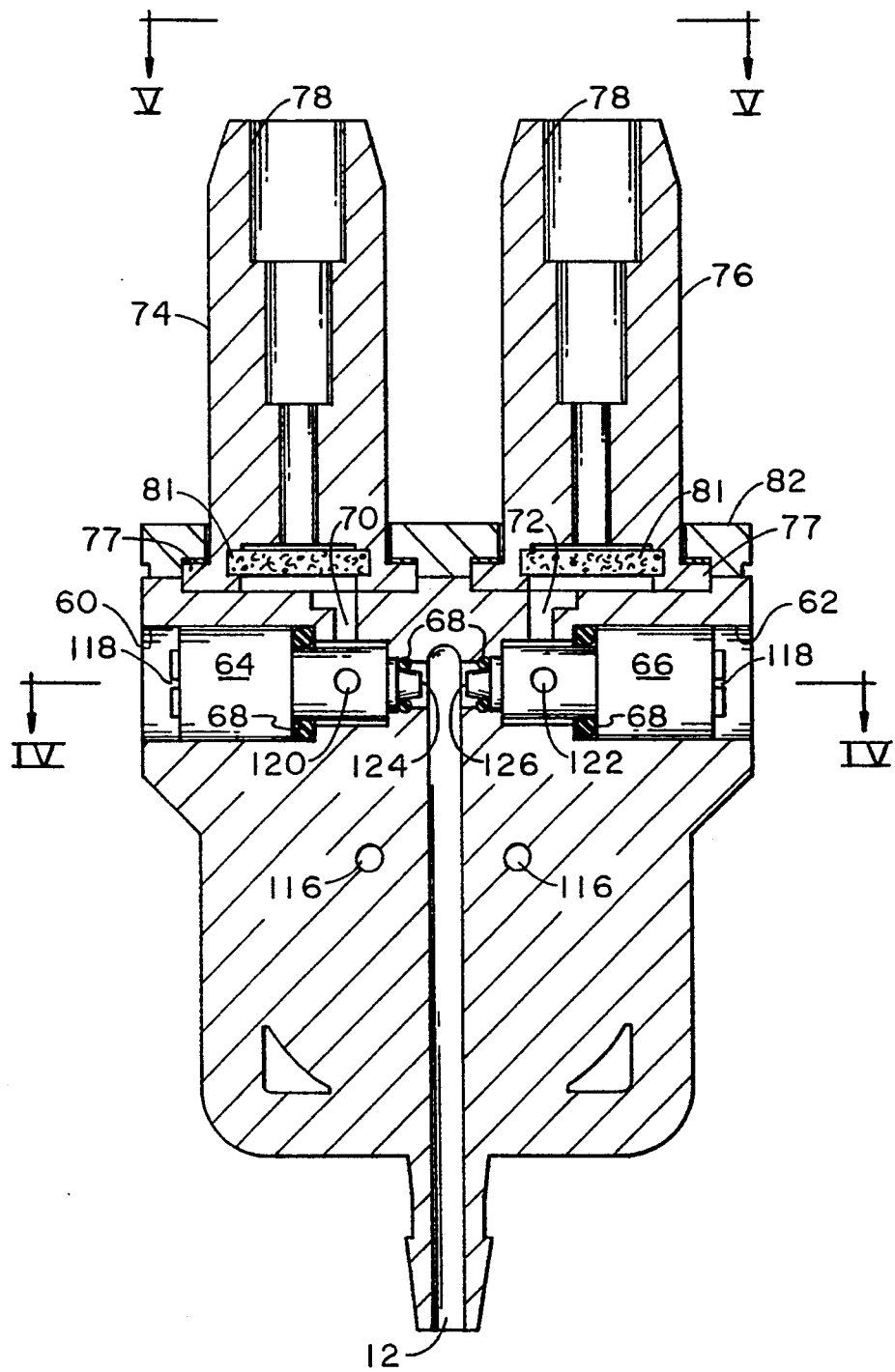
FIG. 3 is a view taken along line III—III of FIG. 1.
Figure 4:
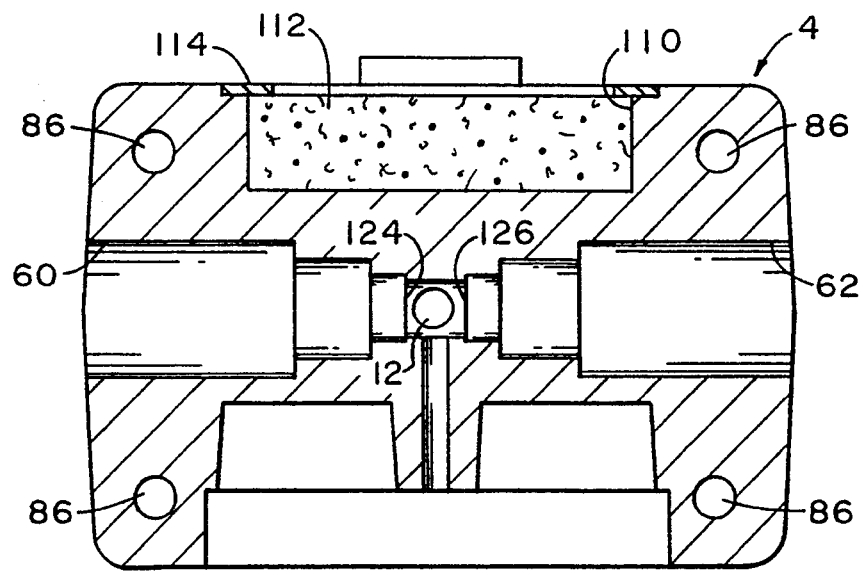
FIG. 4 is a view taken along line IV—IV of FIG. 3.

As perhaps most clearly shown in FIGS. 3 and 4, a pair of opposed valve receptacles 60 and 62 are provided in the regulator body 6. Valve receptacles 60 and 62 communicate with discharge passageway 12 and support adjustable needle valves 64 and 66 which are sealed with respect to the regulator body by O-rings 68. First and second sampling ports 70 and 72 are provided in regulator body 6 and communicate, respectively, with needle valves 64 and 66. O-rings 68 also preclude any external communication of the inlet and outlet ports of the needle valves 64 and 66, so all flow must pass between the needle and seat of each valve. All communication between sampling ports 70 and 72 and discharge passageway 12 is through the needle valves 64 and 66.

Associated with each sampling port is a sample tube holder, one such sample tube holder (reference numeral 74) being operably connected to sampling port 70 and the other sample tube holder 76 being similarly connected to sampling port 72. Sample tube holders 74 and 76, as shown in FIG. 3, include radially outwardly projecting flanges 77 and are preferably provided with internal bores 78 of stepped diameter whereby the holders may accommodate sample tubes of various standard diameters. One such sample tube is represented in phantom line in FIG. 1 and is designated by reference numeral 80. As is known, sample tube 80 typically comprises a hollow tube within which may be contained a suitable sorbent material, e.g., charcoal, silica gel, or Tenax ®/CMS, for collecting organic or inorganic gases and vapors, dusts and particulates, or other airborne contaminants. Each sample tube holder also desirably possesses a filter disk 81 for filtering the air which passes from the sample tube 80 to the regulator 4 through sampling ports 70 and 72.

The means for connecting the sampling tube holders 74 and 76 to the regulator body comprise a sample tube pressure plate 82 which is preferably detachably fastenable to regulator body 6 by screws 84 (FIGS. 2 and 5) which engage with bores 86 (FIGS. 2 and 4) provided in the regulator body. Sample tube pressure plate 82 is provided with first and second bores 88 and 90 of sufficient diameter to accommodate all but the radially protruding flanges 77 of sample tube holders 74 and 76.

Figure 5:
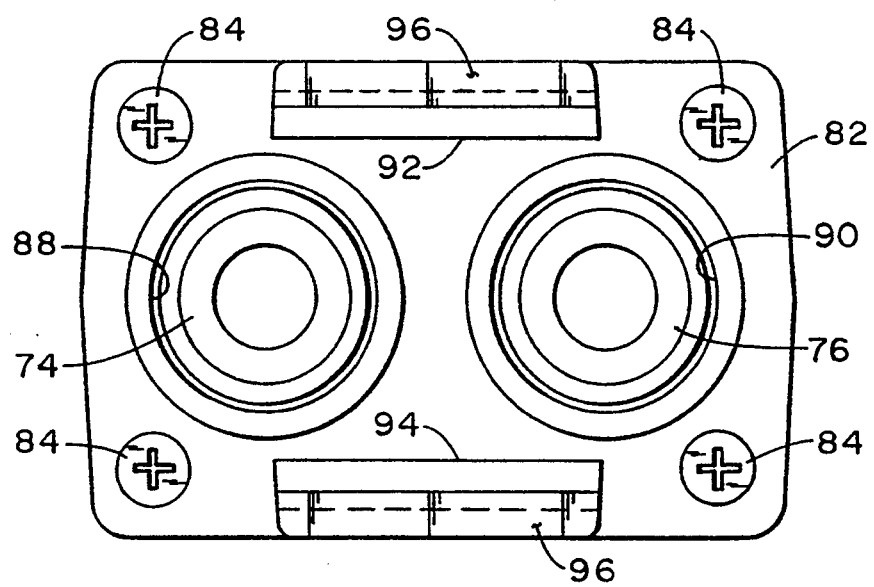
FIG. 5 is a view taken along line V—V of FIG. 3.

As seen in FIGS. 1, 5 and 6, formed integrally with and upwardly extending from the sample tube pressure plate 82 is a pair of latch members 92 and 94 having sloped face surfaces 96 which define retaining shoulders 98. A rigid ventilated sample tube protector 100 is provided for protecting the sample tubes 80 during air sampling. The protector 100 is detachably securable to the sample tube pressure plate 82 and, when attached to the sample tube pressure plate, encloses the sample tubes 80 and sample tube holders 74 and 76. Protector 100 may be of any suitable length depending upon the length of sample tubes 80 to be employed in a particular air particular sampling operation. A pair of engagement openings 102 are provided in opposite walls of the protector 100, which openings are of a size and shape substantially corresponding to that of the sloped face surfaces 96 of latch members 92 and 94. Attachment of the protector 100 to the sample tube pressure plate 82 merely requires placing the open end of the protector over the sample tubes 80, aligning the engagement openings 102 with the latch members 92 and 94 and sliding the protector downwardly along the sloped face surfaces 96, thereby causing inward flexure of same, until the retaining shoulders 98 snap into engagement with the engagement opening 102. When one or both of the sample tubes are to be replaced, detachment of the protector is achieved by applying inwardly directed force (such as by squeezing with the thumb and forefinger) against the sloped face surfaces 96 until the retaining shoulders 98 clear the engagement openings 100 and then sliding the protector upwardly and away from the sample tube pressure plate 82. Air flow through the protector 100 is achieved via a plurality of ports 104 and a fastening means such as a spring clip 106 is desirably carried by the protector to permit the air sampling apparatus 2 to be attached to a worker's clothing during an air sampling test. A similar clip (not illustrated) may be carried by the regulator body at site 108 to enable the apparatus to be suspended from either end thereof.

Referring to FIGS. 1 and 4, a fourth cavity 110 is formed in the regulator body 6 and faces opposite cavities 14, 18 and 22. Cavity 110 is open to the ambient atmosphere. A foam filter 112 is received within cavity 110 and is retained therein by an annular cap ring 114. A pair of ducts 116 (FIGS. 1, 2 and 3) extend between fourth cavity 110 and first cavity 14 so as to permit ambient air flow from the fourth cavity to the first cavity during operation of the air sampling apparatus 2.

The operation of the apparatus is generally as follows. Once the desired sample tubes 80 have been selected and inserted in sample tube holders 74 and 76, the sample tube protector 100 is then attached to the sample tube pressure plate 82, and the conduit 10 is connected to the fitting 8 and the unillustrated remote personal sampling pump. The pump is then activated so as to draw air into the apparatus.

As mentioned previously, needle valves 64 and 66 are adjustable, which adjustability may be suitably effected by engaging the valves with a screwdriver or the like at tool-receivable formations 118 and turning said valves to a selected angular orientation. This recessed screwhead adjustment is preferred to discourage tampering and prevent an accidental change in setting. Alternatively, valves 64 and 66 may be provided with hand-manipulable adjustment knobs. So constructed and arranged, these valves may be independently adjusted so as to regulate the air flow rate through the sampling ports 70 and 72 since the regulator 4 keeps the pressure in discharge passageway 12 at a fixed and constant valve. Needle valves 64 and 66 have valve inlets 120 and 122 and valve outlets 124 and 126. Preferably valve outlets 124 and 126 are directly connected to discharge passageway 12 at the same point so that they are at the same fixed pressure. Depending upon the orientations of the valves 64 and 66, none, some or all of the air which is drawn into the apparatus may pass through the sample tubes 80 and thus sampling ports 70 and 72.

More specifically, when the needle valves 64 and 66 are positioned so as to fully close sampling ports 70 and 72, vacuum created in the first pressure chamber 56 displaces the diaphragm 30 so as to lift stop member 52 from the raised seat 24. Consequently, incoming air enters the foam filter 112 and cavity 110, travels through ducts 116 into first cavity 14, passes through bore 26 and discharge passageway 12 and flows to the personal sampling pump. This is because significant negative pressure acting upon the entire surface of the diaphragm facing first pressure chamber 56 is greater than the counterforce exerted by spring 46 and the minimal negative pressure produced within bore 26 acting in combination to retain the stop member 52 against the raised seat 24.

When the needle valves 64 and 66 are positioned so as to fully open sampling ports 70 and 72, all air drawn into the apparatus passes through ports 104 in the sample tube protector 100, sample tubes 80, sampling ports 70 and 72 and flows directly through discharge passageway 12 to the personal sampling pump. In this condition, the negative pressure in pressure chamber 56 is insufficient to overcome the combined effects of the spring 46 and the vacuum in bore 26. As a result, stop member 52 remains in contact with raised seat 24 whereby no incoming air flows through foam filter 112.

Further, when one or both of the needle valves is positioned to partially open its corresponding sampling port, some of the air drawn into the apparatus enters through the sampling port(s) while the balance enters through the foam filter 112. That is, the vacuum force in pressure chamber 56 is sufficient to lift the stop member 52, however slightly, from the raised seat 24, whereby some air may pass from the first pressure chamber 56 to the discharge passageway 12.

If air is being sampled for more than one contaminant, the air sampling apparatus 2 of the present invention can draw samples through sample tubes 80 containing dissimilar sorbents at independent and different flow rates. In situations where a single contaminant is being sampled, sampling through two sample tubes 80 containing the same sorbent can be performed simultaneously at different flow rates. This type of sampling technique protects against "breakthrough" which occurs when a sample tube's sampling capacity is exceeded because the concentration of the contaminant is higher than expected. If the concentration of the contaminant is higher than anticipated, it can overload the sample tube with the higher flow rate, i.e., a "breakthrough" condition occurs. However, a valid sample can still be obtained from the sample tube operating under the lower flow rate. Conversely, if the contaminant concentration is much less than expected, the air sampling apparatus can provide a valid sample from the sample tube with the higher flow rate.

Alternatively, duplicate sampling using sample tubes containing the same sorbents and operating at the same flow rate can also be conducted to achieve better statistical results with regard to a particular contaminant.

Further, by providing flow rate control at the point of load, i.e., proximate the sampling ports 70 and 72 due to the constant pressure in the discharge passageway 12 at the outlet of the needle valves 64 and 66, rather than at the sampling pump, enhanced control and adjustability is achieved in comparison with presently known air sampling equipment wherein flow control requires an iterative process to set and balance the flows through the sampling ports.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A compact and portable air sampling apparatus adapted for use with a remote vacuum source, said apparatus comprising:

a plurality of sample tube holders;

a regulator incorporated therein including a regulator body having a discharge passageway which is automatically maintained at a constant pressure by the regulator;

one end of said discharge passageway capable of being connected to said remote vacuum source;

a plurality of sampling ports provided in said regulator body and directly connected at the same point to a second end of said discharge passageway;

a plurality of valves provided in said regulator body for controlling communication between said plurality of sampling ports and the second end of said discharge passageway, said plurality of valves being selectively adjustable to simultaneously permit independent air flow rates through each of said plurality of sampling ports; and a means for securing said plurality of sample tube holders to said regulator in cooperative relation with said sampling ports of the regulator body.

2. The apparatus of claim 1 wherein said plurality of valves consist of needle valves.

3. The apparatus of claim 2 wherein said plurality of valves comprise two valves.

4. The apparatus of claim 1 wherein the means for securing said plurality of sample tube holders to said regulator in cooperative relation with said sampling ports is a plate.

5. The apparatus of claim 4 further comprising a ventilated sample tube protector detachably connected to said plate.

6. The apparatus of claim 1 further comprising a clip for suspending said apparatus from a worker's clothing.

7. The apparatus of claim 1 further comprising a flexible diaphragm for defining first and second pressure chambers within said regulator body, a bore in communication with said discharge passageway and said first pressure chamber, another bore in communication with said discharge passageway and said second pressure chamber, duct means for communicating the ambient atmosphere with said second pressure chamber, and means for biasing said diaphragm into contact with said another bore, whereby, when said apparatus is under vacuum produced by said remote vacuum source, adjustment of said plurality of valves creates differential pressures in said first and second pressure chambers effecting positioning of said diaphragm such that air is caused to flow to said discharge passageway via at least one of (1) said duct means and said another bore, and (2) selected ones of said plurality of sampling ports.

8. The apparatus of claim 7 wherein said plurality of valves consist of needle valves.

9. The apparatus of claim 8 wherein said plurality of valves comprise two valves.

10. The apparatus of claim 7 wherein the means for securing said plurality of sample tube holders to said regulator in cooperative relation with said sampling ports is a plate.

11. The apparatus of claim 10 further comprising a ventilated sample tube protector detachably connected to said plate.

12. The apparatus of claim 7 further comprising means for suspending said apparatus from a worker's clothing.

13. A compact and portable air sampling apparatus adapted for use with a remote vacuum source, said apparatus comprising:

a plurality of sample tube holders;

a regulator incorporated therein including a regulator body having a discharge passageway which is automatically maintained at a constant pressure by the regulator;

one end of said discharge passageway capable of being connected to said remote vacuum source;

a plurality of sampling ports provided in said regulator body and communicable with a second end of said discharge passageway;

a plurality of valves provided in said regulator body for controlling communication between said plurality of sampling ports and the second end of said discharge passageway, said plurality of valves being selectively adjustable to simultaneously permit independent air flow rates through each of said plurality of sampling ports; and a plate for securing said plurality of sample tube holders to said regulator in cooperative relation with said sampling ports of the regulator body.

14. The apparatus of claim 13 further comprising a ventilated sample tube protector detachably connected to said plate.

15. The apparatus of claim 13 wherein said plurality of valves consist of needle valves.

16. The apparatus of claim 15 wherein said plurality of valves comprise two valves.

17. The apparatus of claim 13 further comprising means for suspending said apparatus from a worker's clothing.

18. The apparatus of claim 13 further comprising a flexible diaphragm for defining first and second pressure chambers within said regulator body, a bore in communication with said discharge passageway and said first pressure chamber, another bore in communication with said discharge passageway and said second pressure chamber, duct means for communicating the ambient atmosphere with said second pressure chamber, and means for biasing said diaphragm into contact with said another bore, whereby, when said apparatus is under vacuum produced by said remote vacuum source, adjustment of said plurality of valves creates differential pressures in said first and second pressure chambers effecting positioning of said diaphragm such that air is caused to flow to said discharge passageway via at least one of (1) said duct means and said another bore, and (2) selected ones of said plurality of sampling ports.

19. The apparatus of claim 18 further comprising a ventilated sample tube protector detachably connected to said plate.

* * * * *